(12) United States Patent
Schuerfeld et al.

(10) Patent No.: US 8,491,560 B2
(45) Date of Patent: Jul. 23, 2013

(54) DIAPER CLOSURE ELEMENTS

(75) Inventors: Julia Katharina Schuerfeld, Kuerten (DE); Norbert Matthias Stelzer, Bornheim-Hersel (DE)

(73) Assignee: The Procter & Gamble Company, Cincinnati, OH (US)

( * ) Notice: Subject to any disclaimer, the term of this patent is extended or adjusted under 35 U.S.C. 154(b) by 744 days.

(21) Appl. No.: 11/803,218

(22) Filed: May 14, 2007

(65) Prior Publication Data

US 2007/0265592 A1 Nov. 15, 2007

Related U.S. Application Data

(63) Continuation-in-part of application No. PCT/IB2007/050506, filed on Feb. 15, 2007.

(30) Foreign Application Priority Data

Feb. 17, 2006 (EP) .................................... 06003325

(51) Int. Cl.
*A61F 13/15* (2006.01)

(52) U.S. Cl.
USPC ................... 604/392; 604/386; 604/385.01

(58) Field of Classification Search
USPC ............ 604/367, 385.01, 386–387, 389–391, 604/385.03, 392
See application file for complete search history.

(56) References Cited

U.S. PATENT DOCUMENTS

| | | | |
|---|---|---|---|
| 3,860,003 A | | 1/1975 | Buell |
| 4,050,121 A | * | 9/1977 | Richman ................... 24/304 |
| 4,237,890 A | * | 12/1980 | Laplanche ................ 604/390 |
| 4,778,701 A | * | 10/1988 | Pape et al. ................ 428/41.8 |
| B13860003 I5 | | 4/1989 | Buell |
| 4,834,735 A | | 5/1989 | Alemany et al. |
| B23860003 I5 | | 6/1990 | Buell |
| 5,037,416 A | | 8/1991 | Allen et al. |

(Continued)

FOREIGN PATENT DOCUMENTS

| | | |
|---|---|---|
| EP | 603325 B1 | 5/1996 |
| EP | 0 752 239 B1 | 4/2000 |

(Continued)

OTHER PUBLICATIONS

International Search Report.

*Primary Examiner* — Michele M Kidwell
(74) *Attorney, Agent, or Firm* — Thibault Fayette; Laura A. Whitmer (57) ABSTRACT

A diaper comprising a garment facing side and a wearer facing side, the diaper further comprising closure elements, at least one closure element comprising:

a carrier layer (1) comprising a nonwoven or woven material, and comprising a first surface and a second surface opposite the first surface, a first side edge and a second side edge opposite the first side edge, and a first end edge and a second end edge opposite the first end edge, the first surface of the carrier layer (1) comprising a bonding layer (2), the bonding layer (2) not extending over the entire first surface of the carrier layer (1) and the first surface of the carrier layer (1) further comprising an anchoring layer (3) suitable for the attachment of a hook patch (5), the second surface of the carrier layer (1) comprising a separation layer (4).

A closure element and a method of manufacture are further aspects of the invention.

7 Claims, 4 Drawing Sheets

U.S. PATENT DOCUMENTS

| | | |
|---|---|---|
| 5,151,092 A | 9/1992 | Buell et al. |
| 5,269,775 A | 12/1993 | Freeland et al. |
| 5,569,234 A | 10/1996 | Buell et al. |
| 5,599,601 A * | 2/1997 | Polski et al. .................. 428/40.1 |
| 5,625,222 A | 4/1997 | Yoneda et al. |
| 5,759,317 A * | 6/1998 | Justmann ........................ 156/66 |
| 5,876,531 A | 3/1999 | Jacobs et al. |
| 6,004,306 A | 12/1999 | Robles et al. |
| 6,461,715 B1 | 10/2002 | Guenther et al. |
| 6,719,744 B2 * | 4/2004 | Kinnear et al. ............... 604/389 |

FOREIGN PATENT DOCUMENTS

| | | |
|---|---|---|
| EP | 1 543 807 A1 | 6/2005 |
| IE | 59781 B | 4/1994 |
| WO | WO-96/02218 A2 | 2/1996 |
| WO | WO-01/68025 A1 | 9/2001 |
| WO | WO-2007/050506 A1 | 5/2007 |

* cited by examiner

DIAPER CLOSURE ELEMENTS

CROSS REFERENCE TO RELATED APPLICATIONS

This application is a continuation in part application of prior copending International Application No. PCT/IB2007/050506, filed Feb. 15, 2007, designating the U.S., which claims priority to European Patent Application No. 0603325.5, filed on Feb. 17, 2006, the substances of which are incorporated herein by reference.

FIELD OF THE INVENTION

The present invention relates to absorbent articles such as disposable diapers, and diaper-like incontinence products. More specifically, the present invention relates to a closure element which can be used for a fastening system for such an article.

BACKGROUND OF THE INVENTION

Disposable absorbent articles are broadly available and consumers are used to a high performance. However, consumers do not only expect superior absorbency behaviour, but place more and more emphasis on the wearing comfort of such articles, and namely on good and reliable fit. Nevertheless, these articles must be relatively inexpensive.

The present invention provides a closure element with a carrier layer made of a non-woven material, wherein a bonding layer is applied onto the first/top side of the carrier layer to connect the carrier layer with a diaper chassis, and wherein a (non-sticky) separation layer is applied to the bottom/second side of the carrier layer. A hook patch that serves to close the diaper can be provided on the first/top side of the carrier layer. Further the present invention provides a diaper comprising such closure element(s) and provides a method to manufacture such a closure element.

The known closure elements in the field that have a non-woven carrier layer often have the problem that the hook patch does not sufficiently adhere to the first/top side of the carrier layer. Due to the open-pored first/top side of the surface of the non-woven material, the contact area for adhesion is small. Thus, such adhesion often fails even at low shear loads. For this reason, the non-woven material is usually coated with an extrusion layer on one side. The smooth sheet surface of the extrusion layer side provides for superior adhesion of the e.g. the self-sticking hook patch. However, due to the complete surface coating, the manufacturing of such a closure element is expensive.

The present invention provides a closure element with a carrier layer made of a non-woven material that can be manufactured with reasonable expense.

In a further aspect the present invention provides an absorbent article, which is more comfortable to wear, and which in particular provides superior and reliable fit.

In a yet further aspect, the present invention provides a method for manufacturing such closure elements.

SUMMARY OF THE INVENTION

The present invention relates to a diaper comprising a garment facing side and a wearer facing side, the diaper further comprising closure elements, at least one closure element comprising:
a carrier layer (1) comprising a non-woven or woven material, and comprising a first surface and a second surface opposite the first surface, a first side edge and a second side edge opposite the first side edge, and a first end edge and a second end edge opposite the first end edge,
the first surface of the carrier layer (1) comprising a bonding layer (2), the bonding layer (2) not extending over the entire first surface of the carrier layer (1) and the first surface of the carrier layer (1) further comprising an anchoring layer (3) suitable for the attachment of a hook patch (5),
the second surface of the carrier layer (1) comprising a separation layer (4).

Further, the present invention relates to a closure element suitable to be used for a diaper, the closure element comprising
a carrier layer (1) comprising a non-woven material, and comprising a first surface and a second surface opposite the first surface, a first side edge and a second side edge opposite the first side edge, and a first end edge and a second end edge opposite the first end edge,
the first surface of the carrier layer (1) comprising a bonding layer (2), the bonding layer (2) not extending over the entire first surface of the carrier layer (1) and the first surface of the carrier layer (1) further comprising an anchoring layer (3) suitable for the attachment of a hook patch (5),
the second surface of the carrier layer (1) comprising a separation layer (4).

Yet further, the present invention relates to a method for manufacturing at least one closure element, comprising the steps of:
providing a carrier layer (1) comprising a non-woven material, and comprising a first surface and a second surface opposite the first surface, a first side edge and a second side edge opposite the first side edge, and a first end edge and a second end edge opposite the first end edge,
providing a bonding layer (2) and attaching the bonding layer (2) to the first surface of the carrier layer (1) such that the bonding layer (2) does not extend over the entire first surface of the carrier layer (1),
providing an anchoring layer (3) and attaching the anchoring layer (3) suitable for the attachment of a hook patch (5) to the first surface of the carrier layer (1),
attaching a separation layer (4) to the second surface of the carrier layer (1).

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Definitions

As used herein, the following terms have the following meanings:

"Diaper" refers to devices that absorb and contain liquid, essentially faeces and urine, and that are worn by infants and incontinent persons about the lower torso. These devices include but are not limited to disposable devices, tape diapers, adult incontinent briefs, training pants, diaper holders and liners, and the like.

"Disposable" is used herein to describe articles that are generally not intended to be laundered or otherwise restored or reused i.e., they are intended to be discarded after a single use and, possibly, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

"Attached" or "Joined" encompasses configurations whereby an element is directly secured to another element by affixing the element directly to the other element, and configurations whereby an element is indirectly secured to another element by affixing the element to (an) intermediate member(s) which in turn is/are affixed to the other element. "Directly" attaching or joining does not encompass the intermediate attaching or joining via another identifiable element or layer.

"Comprise," "comprising," and "comprises" is an open ended term that specifies the presence of what follows e.g. a component but does not preclude the presents of other features, elements, steps or components known in the art, or disclosed herein.

The terms "fiber" and "filament" are used interchangeably.

The terms "nonwoven", "nonwoven fabric" and "nonwoven web" are used interchangeably.

Absorbent Articles

Figure 1:
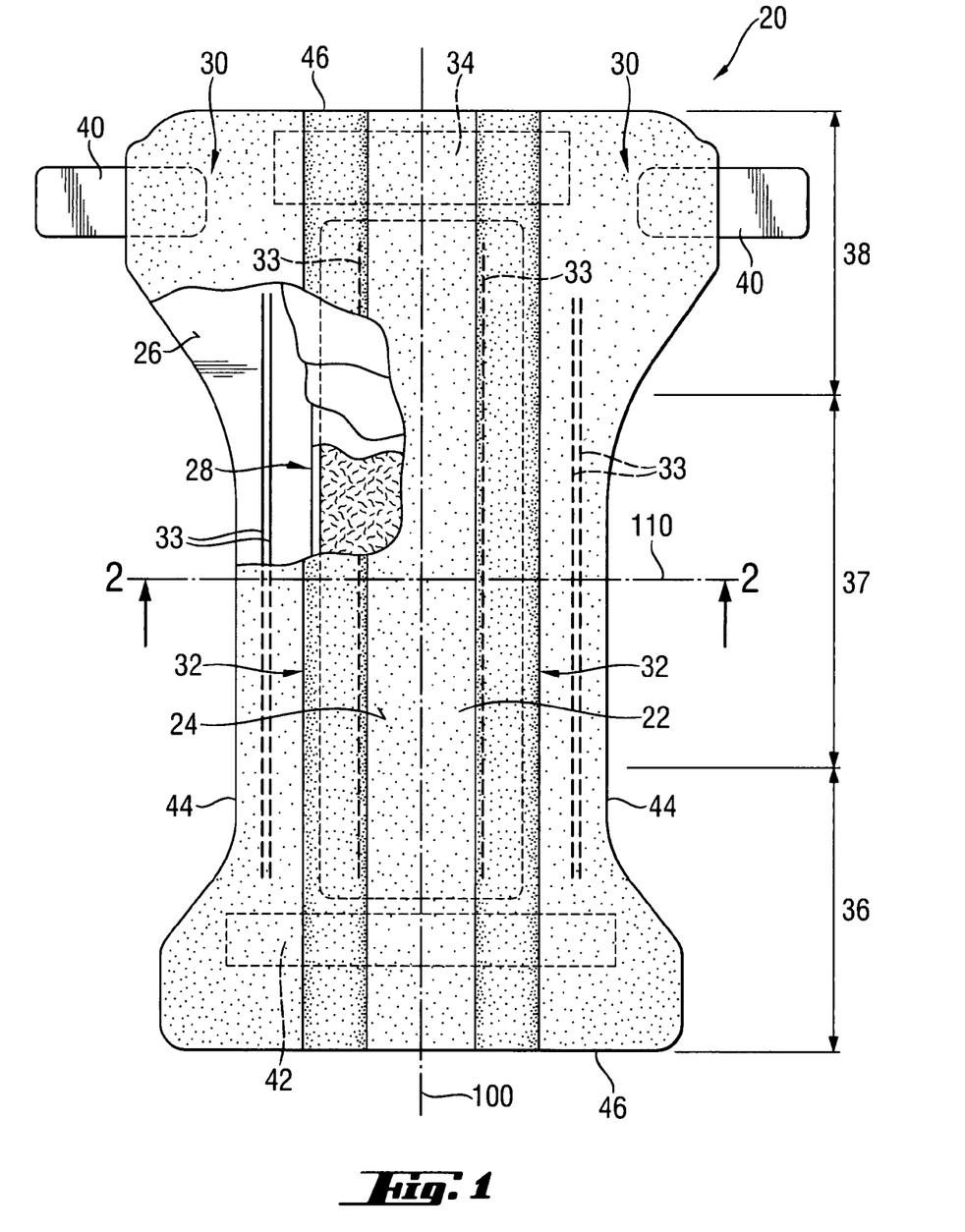
FIG. 1 is a top plan view of a disposable diaper, with the upper layers partially cut away.

FIG. 1 is a plan view of a diaper 20 as an embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis can further include side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 attached to the rear waist region 38 and comprising a landing zone 42 attached to the front waist region 36. The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. The topsheet 24, the backsheet 26, and the absorbent core 28 may be assembled in a variety of well-known configurations. Specific diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. Often, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 attached to the rear waist region 38. In one embodiment the fastening system further comprises a landing zone 42 attached to the front waist region 36. In another embodiment the landing zone 42 is provided in the rear waist region 38 and fastening members 40 are provided in the front waist region 36.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. In some embodiments, the materials making up the fastening device are flexible. The flexibility is designed to allow the fastening system to conform to the shape of the body and thus, reduces the likelihood that the fastening system will irritate or injure the wearer's skin.

Figure 2:
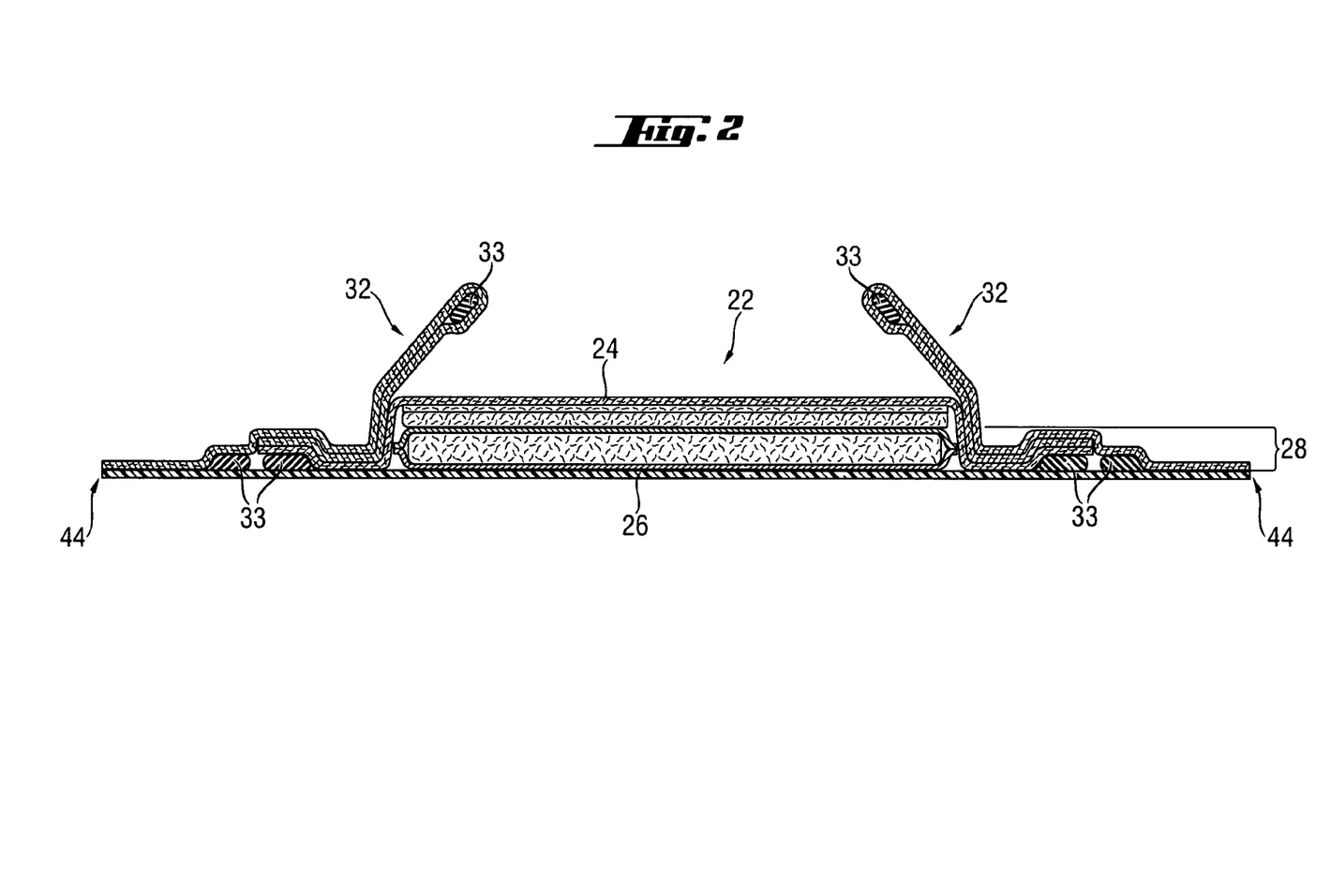
FIG. 2 is a cross-sectional view of the disposable diaper shown in FIG. 1.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core may comprise an acquisition system 50, which comprises an upper acquisition layer 52 facing towards the wearer and a lower acquisition layer 54. In one embodiment the upper acquisition layer comprises a nonwoven fabric whereas the lower acquisition layer comprises a mixture of chemically stiffened, twisted and curled fibers, high surface area fibers and thermoplastic binding fibers. In another embodiment both acquisition layers are provided from a non-woven material, which can also be hydrophilic. The acquisition layer can be in direct contact with the storage layer 60.

Acquisition members according to the present invention may comprise the acquisition system 50 of a diaper as described. In one embodiment, the acquisition members are comprised by the upper acquisition layer 52. In one embodiment of the present invention the upper acquisition layer 52 consists of the claimed acquisition member.

The storage layer 60 can be wrapped by a core wrap material. In one embodiment the core wrap material comprises a top layer 56 and a bottom layer 58. The top layer 56 and the bottom layer 58 can be provided from a non-woven material. One useful material is a so-called SMS material, comprising a spunbonded, a melt-blown and a further spunbonded layers. The top layer 56 and the bottom layer 58 may be provided from two or more separate sheets of materials or they may be alternatively provided from a unitary sheet of material. Such a unitary sheet of material may be wrapped around the storage layer 60, e.g. in a C-fold. The top layer 56 and the bottom layer 58 may also be joined to each other, for example along their periphery. In another option both layers are joined along their longitudinal peripheries, in other embodiments they are joined along the transversal peripheries, or along the longitudinal and the transversal peripheries. The joining can be achieved by multiple means well known in the art, eg. by adhesive means, using a continuous or a discontinuous pattern, for example a linear or curvilinear pattern.

The storage layer 60 typically comprises fibrous materials, mixed with superabsorbent gelling materials. Other materials described above as suitable for the absorbent core 28 may also be comprised.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, or carding. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Man-made fibers can either be synthetic fibers or they can be derived from natural fibers. Examples of man-made fibers, which are not synthetic but which are derived from natural fibers, include but are not limited to rayon and lyocell (tradename "Tencel"®), both of which are derived from cellulose, a natural polysaccharide fiber. Synthetic fibers, which are not derived from natural fibers, can be derived from other natural sources or from mineral sources. Example synthetic fibers not derived from natural sources include but are not limited to polysaccharides such as starch. Example synthetic fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electro spinning, and combinations thereof.

Examples of "laying" processes include wet-laying and air-laying (the latter occasionally also referred to as dry-laying). Examples of air-laying processes include but are not limited to airlaying, carding, and combinations thereof typically forming layers. Combinations of the above processes yield nonwovens commonly called hybrids or composites. Examplary combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

All of the above described fibers and manufacturing techniques can be useful for providing an acquisition member according to the present invention.

Closure Elements

Figure 4:
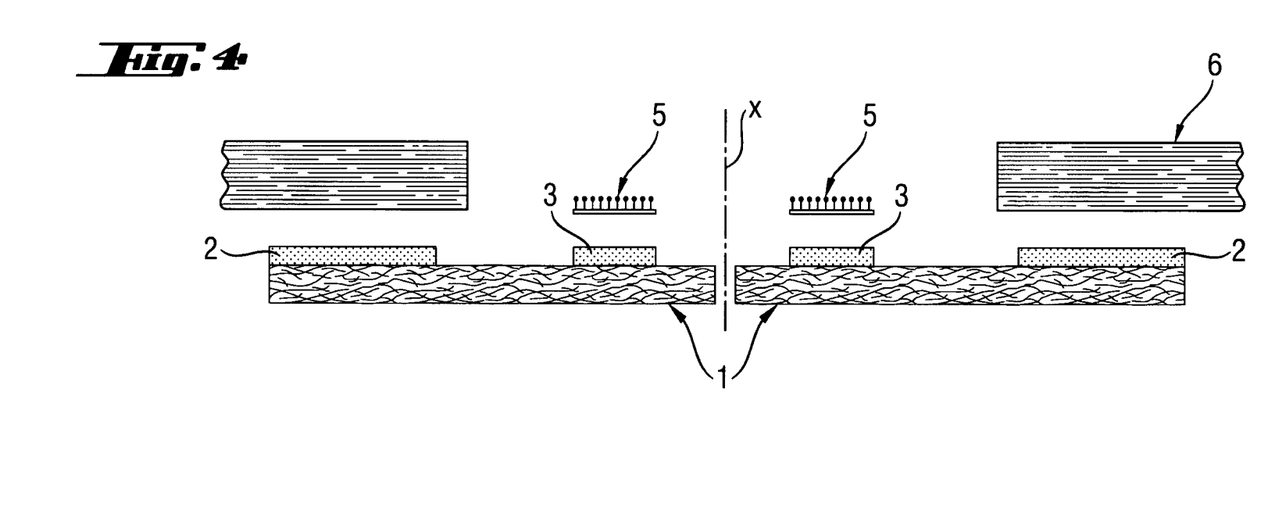
FIG. 4 is a cross-sectional view of a web comprising closure elements according to the present invention illustrating the attachment of the closure element to a diaper and the attachment of a hook patch to the closure element.

Closure elements according to the present invention comprise a carrier layer. This carrier layer can be provided from a woven or a non-woven piece of material, typically a strip of material, such as a small rectangular strip of material. The carrier layer will comprise two end edges. As used herein, "end edge" refers each one of those edges which provide, in the configuration in which the closure element is to be attached to a diaper, the proximal edge (in the vicinity of which the closure element is attached to the diaper) and the distal edge (in the vicinity of which the tape is handled by a user). If the carrier layer is provided in the form of an essentially rectangular strip of material, this strip will comprise two shorter edges, which can provide the end edges, and two longer edges, which can provide the side edges. The end edges can have a length between 5 mm and 50 mm, or 10 mm and 40 mm, or 25 mm and 35 mm. The side edges can have a length of 20 mm to 150 mm, or 30 mm to 100 mm, or 40 mm to 70 mm. Such a rectangular strip is shown in FIG. 4, where one end edge is attached to the diaper and forms the proximal edge and the other end edge froms the distal end of the carrier layer at which the carrier layer and the closure element can be gripped.

The carrier layer can be provided from a variety of fibers as mentioned above as being useful for non-woven fabrics, namely from thermoplastic fibers, polyethylene fibers and polypropylene fibers. Spunbond non-woven materials have been found suitable. The material used for the carrier layer can be a non-stretchable material or a stretchable material, or a stretchable and elastic material.

The material can have a basis weight from 10 g/m to 300 g/m² or from 20 g/m² to 200 g/m², or 40 g/m² to 100 g/m², or 60 g/m² to 80 g/m².

The bonding layer (2) serves for the attachment of the closure element to an absorbent article. This attachment can be any attachment common in the art, such as a mechanical attachment, for example crimping, or an adhesive attachment or a combination thereof. Hot-melt adhesives have been found suitable for the adhesive attachment. The basis weight of an adhesive layer comprised by the bonding layer 2 can be from 5 to 100 g/m², or from 10 to 60 g/m², or from 20 to 50 g/m².

Figure 3:
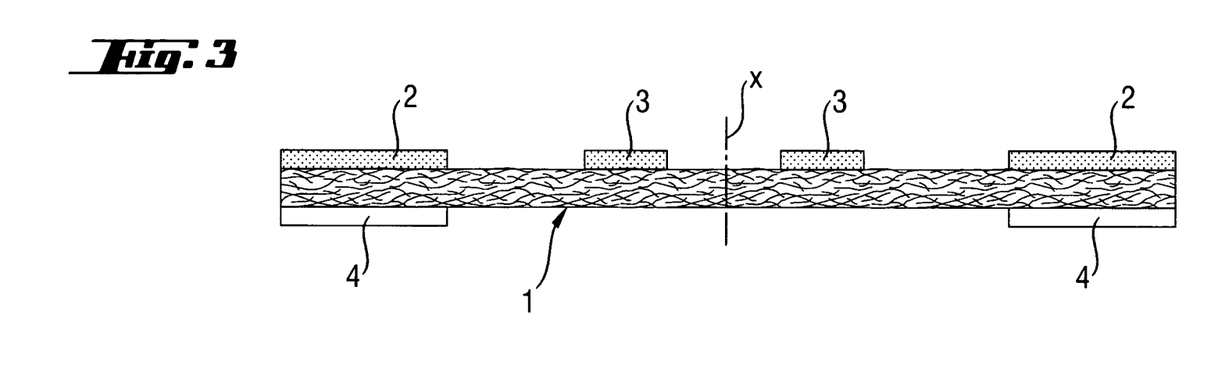
FIG. 3 is a cross-sectional view of an intermediate layer for the manufacturing of a closure element according to the present invention.

Suitable hot-melt adhesives can easily be attached to the absorbent article, for example the backsheet of the absorbent article. While the adhesiveness of the hot-melt adhesive may increase with temperature, it is preferred for the bonding layer that sufficient adhesiveness is provided at room temperature. In view of any potential room temperature adhesion, it is considered an advantage to not expose any surface of the bonding element, and in particular not any adhesive surface of the bonding element, when the closure element is provided in the ready-to-use configuration on a diaper. According to the present invention the bonding layer does not extend over the entire first surface of the carrier layer. If other elements are provided on the first surface of the carrier layer, in one option, the bonding layer is provided such that it does not overlap with other such elements. In one option, the bonding layer is provided on the first surface of the carrier layer at a distance to any other elements provided thereon, namely at a distance to an anchoring layer (3) provided thereon. In one embodiment, the bonding layer (2) is provided adjacent to a first end edge of the carrier layer and other elements, for example the anchoring layer (3) are provided adjacent to the second, opposing end edge of the carrier layer. Such an embodiment is shown in FIG. 3.

An anchoring layer (3) is suitable to facilitate the attachment of a fastening means, such as a hook patch to the carrier layer. An anchoring layer (3) can be provided from a variety of materials, including thermoplastics resins and hot-melt adhesive. Such materials are bonded either mechanically or chemically or via both methods to the carrier layer, which typically has a porous surface. The anchoring layer (3) can be directly attached to the carrier layer (1). The surface of the anchoring layer (3) opposite the carrier layer facing surface can be optimized for the attachment of a fastening means. For example, a smooth surface can be provided. The surface can also be provided with an adhesive layer for such attachment purposes. In other embodiments no adhesive layer is provided on the anchoring layer (3), but the hook patch (5) comprises a fastening material, for example in the form of a layer of hot-melt adhesive. The anchoring layer (3) may provide a low to zero adhesive force at room temperature or may comprise some residual tackiness/adhesive force at room temperature. This adhesive force at room temperature or at manufacturing temperature (which, however, is normally room temperature) will influence the need to cover the anchoring layer (3) with a dedicated separation layer.

The anchoring layer (3) can be provided on the first surface of the carrier layer (1) but at a distance to the bonding layer (2). It is not necessary that the anchoring layer (3) spans over the whole length extension of the carrier layer (1)—thereby the present invention can achieve meaningful cost savings as compared to the prior art in the field. In one embodiment, the lengthwise extension of the anchoring layer (3) is equal to or less than (e.g. 10% or 20% less than) the lengthwise extension of the hook patch (5). The anchoring layer (3) may span over the whole width extension of the carrier layer (1) by spanning from the first side edge to the second side edge.

Figure 5:
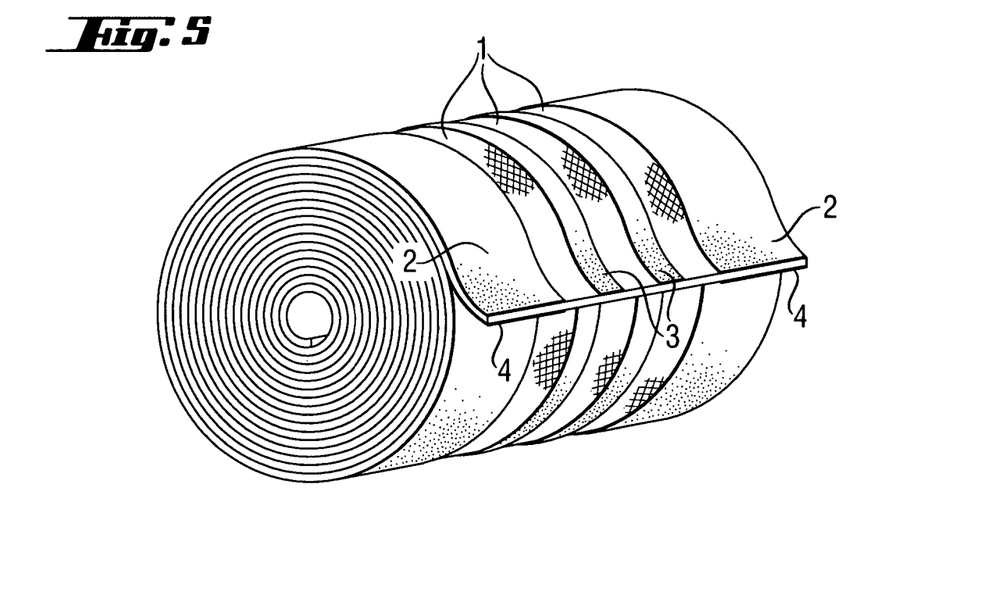
FIG. 5 is a perspective view of an intermediate product as depicted in FIG. 1 in the rolled up state.
Figure 6:
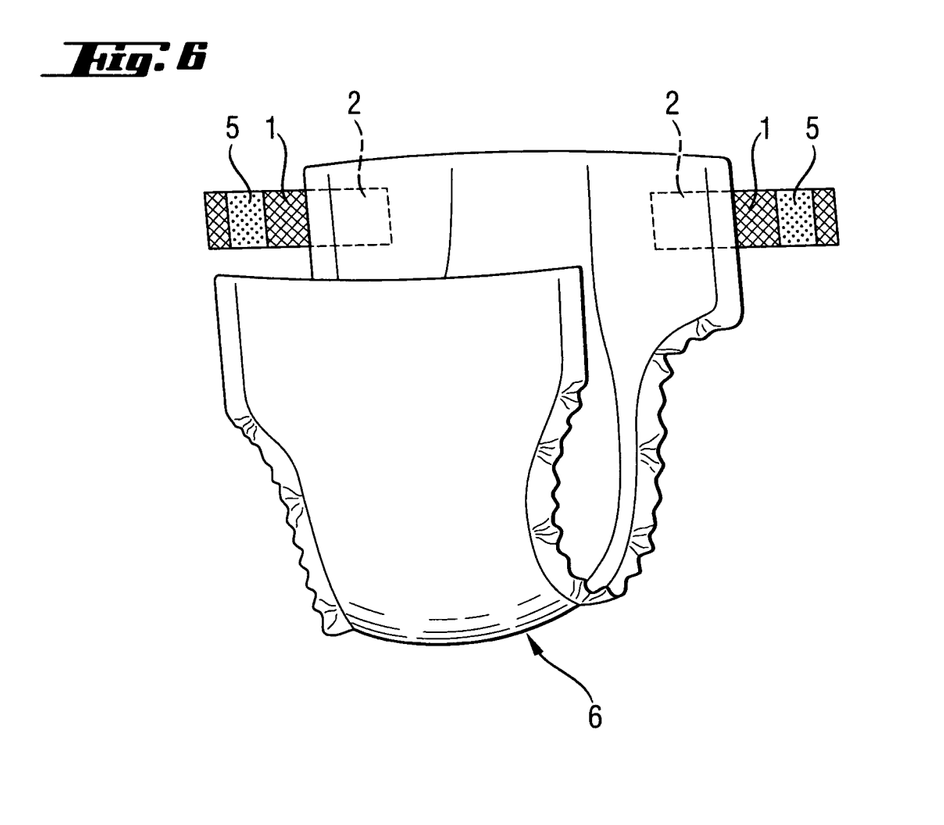
FIG. 6 is a perspective view of a tape diaper comprising two closure elements according to the present invention.

One or more separation layers can be provided to prevent premature or unintentional attachment of adhesive surfaces. Such separation layers can be provided, for example, when a web material comprising closure elements is rolled up as shown in FIG. 5. According to the present invention the second surface of the carrier layer comprises at least one separation layer (4). The separation layer (4) may be provided opposite to and extending over essentially the same area as the bonding layer. This is shown, for example, in FIG. 3. A further separation layer can be provided on the second surface of the carrier layer, for example opposite to and extending over essentially the same area as the anchoring layer (3). This further separation layer can further facilitate the easy and reliable unwinding of a role comprising closure elements, in particular if the anchoring layer (3) exhibits a residual tackiness at the temperature at which the role is to be unwound.

The separation layer can be provided from any material known in the art, in one option the separation layer is provided in the form of a silicone layer.

One suitable method of manufacturing at least one closure element comprises the following steps:
- providing a carrier layer 1 comprising a non-woven material, and comprising a first surface and a second surface opposite the first surface, a first side edge and a second side edge opposite the first side edge, and a first end edge and a second end edge opposite the first end edge,
- providing a bonding layer 2 and attaching the bonding layer 2 to the first surface of the carrier layer 1 such that the bonding layer 2 does not extend over the entire first surface of the carrier layer 1,
- providing an anchoring layer 3 and attaching the anchoring layer 3 suitable for the attachment of a hook patch 5 to the first surface of the carrier layer 1,
- attaching a separation layer 4 to the second surface of the carrier layer 1.

Optionally, such a method of manufacturing also comprises a step of attaching a hook patch to each closure element.

It is often economical to start from one web of carrier material and to produce an intermediate web comprising a multitude of closure elements, from which closure elements can be provided by severing that intermediate web. When starting from a web of carrier layer material, for example a non-woven web, the bonding layer (2) can be provided from a strip of bonding layer material, and the anchoring layer (3) can be provided from a continuous strip of anchoring material, and likewise the at least one separation layer can be provided from a continuous strip of separation layer material. In one method of manufacturing a single web of non-woven material is provided and two webs of bonding layer material, two webs of anchoring layer (3) material and two webs of separation layer material are provided. An intermediate product as obtained from such economic process of manufacture is shown in FIGS. 3 to 5. In one embodiment, such an intermediate material comprising a multitude of closure elements as claimed is symmetrical about a central axis. This axis of symmetry will then define a severing/cutting line, along which the web needs to be severed/cut as to finally obtain single closure elements. For transport purposes such an intermediate web can be rolled up, see FIG. 5. In the rolled up stage separation layers, such as separation layer (4) will prevent the adhesion of the bonding layers (2), and potentially of the anchoring layers (3) to other portions of the web.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rolled strip of closure elements that are suitable to be used for a diaper, the rolled strip of closure elements comprising
   a carrier layer comprising a non-woven material, said carrier layer having a first surface and a second surface opposite the first surface, a first side edge and a second side edge opposite the first side edge, a longitudinal axis and a first end edge and a second end edge opposite the first end edge,
   a first bonding layer disposed on said first surface of the carrier layer and proximate said first end edge, the first bonding layer not extending over the entire first surface of the carrier layer;
   a second bonding layer disposed on said first surface of the carrier layer and proximate said second end edge, the second bonding layer not extending over the entire first surface of the carrier layer wherein said first and second bonding layers are disposed on opposite sides of said carrier layer relative to the longitudinal axis of said carrier layer;
   a first anchoring layer disposed on said first surface of the carrier layer and proximate said longitudinal axis, wherein said first anchoring layer is suitable for the attachment of a hook patch, the first anchoring layer not extending over the entire first surface of the carrier layer;
   a second anchoring layer disposed on said first surface of the carrier layer and proximate said longitudinal axis, wherein said second anchoring layer is suitable for the attachment of a hook patch, the second anchoring layer not extending over the entire first surface of the carrier layer, wherein said first and second anchoring layers are disposed on opposite sides of said carrier layer relative to the longitudinal axis of said carrier layer;
   a first separation layer disposed on said second surface of said carrier layer such that said first separation layer is disposed opposite said first anchoring layer; and
   a second separation layer disposed on said second surface of said carrier layer such that said first separation layer is disposed opposite said second anchoring layer wherein said first and second separation layers are disposed on opposite sides of said carrier layer relative to the longitudinal axis of said carrier layer and wherein said first and second separation layers comprise a silicone layer;

wherein said carrier layer is rolled such that first separation layer contacts said first bonding layer, and said second separation layer contacts said second bonding layer.

2. The rolled strip of closure elements of claim 1 wherein the bonding layers are provided in the form of an adhesive layer.

3. The rolled strip of closure elements of claim 2 wherein said adhesive layers are provided from a hot melt adhesive.

4. The rolled strip of closure elements according to claim 1 wherein said anchoring layers are directly attached to the carrier layer.

5. The rolled strip of closure elements according to claim 1 wherein the bonding layers are directly attached to the carrier layer.

6. The rolled strip of closure elements according to claim 1 wherein the anchoring layers are non-adhesive at room temperature.

7. The rolled strip of closure elements according to claim 1 wherein the carrier layer is provided from polypropylene and has a basis weight from about 40 g/m² to about 100°/m.

* * * * *

UNITED STATES PATENT AND TRADEMARK OFFICE
CERTIFICATE OF CORRECTION

PATENT NO.        : 8,491,560 B2
APPLICATION NO.   : 11/803218
DATED             : July 23, 2013
INVENTOR(S)       : Schuerfeld et al.

Page 1 of 1

It is certified that error appears in the above-identified patent and that said Letters Patent is hereby corrected as shown below:

In the Claims:

Column 11, Line 20, please replace "about 100°/m" with -- about 100 $g/m^2$ --

Signed and Sealed this
Seventeenth Day of September, 2013

Teresa Stanek Rea
*Deputy Director of the United States Patent and Trademark Office*